(12) United States Patent
Higgins et al.

(10) Patent No.: US 12,426,915 B2
(45) Date of Patent: Sep. 30, 2025

(54) DEVICES AND METHODS FOR GENERATING ORBITAL MOTION IN DRIVE SHAFTS FOR ROTATIONAL MEDICAL DEVICES

(71) Applicant: Cardiovascular Systems, Inc., St. Paul, MN (US)

(72) Inventors: Joseph P. Higgins, Minnetonka, MN (US); Kayla J. Eichers, Richfield, MN (US); Jeffrey R. Stone, Minnetonka, MN (US)

(73) Assignee: Cardiovascular Systems, Inc., St. Paul, MN (US)

( * ) Notice: Subject to any disclaimer, the term of this patent is extended or adjusted under 35 U.S.C. 154(b) by 0 days.

(21) Appl. No.: 18/235,570

(22) Filed: Aug. 18, 2023

(65) Prior Publication Data

US 2024/0032960 A1   Feb. 1, 2024

Related U.S. Application Data

(63) Continuation of application No. 16/594,883, filed on Oct. 7, 2019, now Pat. No. 11,730,509.

(60) Provisional application No. 62/742,705, filed on Oct. 8, 2018.

(51) Int. Cl.
*A61B 17/3207*  (2006.01)
*A61B 17/32*    (2006.01)

(52) U.S. Cl.
CPC ............... *A61B 17/320758* (2013.01); *A61B 17/320725* (2013.01); *A61B 2017/320004* (2013.01);
(Continued)

(58) Field of Classification Search
CPC .... A61B 17/320758; A61B 17/320725; A61B 2017/320004; A61B 2017/320032; A61B 2017/320766
See application file for complete search history.

(56) References Cited

U.S. PATENT DOCUMENTS 5,314,438 A   5/1994   Shturman
5,533,987 A   7/1996   Pray et al.
(Continued)

FOREIGN PATENT DOCUMENTS

WO   2018075545 A1   4/2018

OTHER PUBLICATIONS

Notification Concerning Transmittal of International Preliminary Report on Patentability and International Preliminary Report on Patentability issued in PCT Application No. PCT/US2019/055122 dated Apr. 22, 2021.
(Continued)

*Primary Examiner* — Ashley L Fishback
(74) *Attorney, Agent, or Firm* — Kagan Binder, PLLC (57) ABSTRACT

Devices, methods and systems are described that enable achieving a working diameter that is greater than a resting diameter and to stimulate fluid circulation during high-speed rotation. The drag coefficient of the drive shaft is increased and, in some embodiments, the mass is increased. Among other advantages, the resulting drive shaft with an eccentric element integrated with and/or attached thereto will achieve orbital motion at a rotational speed that is less the rotational speed required to achieve orbital motion without the increased drag coefficient. The concomitant increase in fluid flow and/or fluid stirring at a comparatively lower rotational speed is a further advantage. These characteristics may allow, therefore, a smaller diameter abrasive element to be used which is advantageous in small and/or highly tortuous vessels.

6 Claims, 7 Drawing Sheets

(52) U.S. Cl.
CPC ............. *A61B 2017/320032* (2013.01); *A61B 2017/320766* (2013.01)

(56) References Cited

U.S. PATENT DOCUMENTS

| | | |
|---|---|---|
| 5,554,163 A | 9/1996 | Shturman |
| 5,897,566 A | 4/1999 | Shturman et al. |
| 5,925,055 A | 7/1999 | Adrian et al. |
| 6,146,395 A | 11/2000 | Kanz et al. |
| 8,597,313 B2 | 12/2013 | Thatcher et al. |
| 2003/0139689 A1 | 7/2003 | Shturman et al. |
| 2009/0018564 A1 | 1/2009 | Shturman |
| 2009/0264908 A1 | 10/2009 | Kallok |
| 2011/0009888 A1 | 1/2011 | Shturman |
| 2013/0035665 A1 | 2/2013 | Chu et al. |
| 2015/0196320 A1 | 7/2015 | Robinson et al. |
| 2016/0183968 A1 | 6/2016 | Cambronne |
| 2016/0279388 A1 | 9/2016 | Barrish et al. |
| 2017/0290603 A1 | 10/2017 | Piippo Svendsen et al. |
| 2018/0235652 A1 | 8/2018 | Benjamin et al. |

OTHER PUBLICATIONS

International Search Report and Written Opinion Issued in PCT application No. PCT/US2019/55122, dated Mar. 4, 2020.
International Search Report and Written Opinion Issued in PCT application No. PCT/US2019/55118, dated Mar. 5, 2020.
Extended European Search Report issued in related EP Application No. 19870850.5, dated May 17, 2022.

DEVICES AND METHODS FOR GENERATING ORBITAL MOTION IN DRIVE SHAFTS FOR ROTATIONAL MEDICAL DEVICES

CROSS-REFERENCE TO RELATED APPLICATIONS

This application is a continuation application of U.S. Ser. No. 16/594,883, filed Oct. 7, 2019, now allowed, which claims the benefit of U.S. Provisional Application No. 62/742,705, filed Oct. 8, 2018 and entitled PREFORMED DRIVE SHAFT FOR ROTATIONAL MEDICAL DEVICES WITH NODE ANTI-NODE AND FLUID STIRRING ELEMENTS, the contents of which are incorporated herein by reference in their entireties for all purposes.

STATEMENT REGARDING FEDERALLY SPONSORED RESEARCH OR DEVELOPMENT

Not Applicable

BACKGROUND OF THE INVENTION

Field of the Invention

The invention relates to drive shafts used in rotational medical devices including but not limited to orbital atherectomy devices and systems.

Description of the Related Art

Rotational medical devices require a drive shaft that is rotated at high rotational speeds. For rotational atherectomy devices, it is known that adding an abrasive element to the drive shaft, wherein the abrasive element has a center of mass radially offset from the longitudinal axis of the drive shaft will achieve orbital motion during high-speed rotation. One of the characteristics of orbital motion is a working diameter achieved by the abrasive element during high-speed rotation that is greater than a resting diameter of the abrasive element. In these known systems, the abrasive element having a radially offset center of mass is referred to as "eccentric." This eccentricity in terms of the radially offset center of mass is achieved in known devices using a geometric asymmetry of the abrasive element, an asymmetric mounting of the abrasive element to the drive shaft and/or moving the center of mass of a symmetric abrasive element by, e.g., inserting a high-density plug of material into the abrasive element and/or removing some material from the abrasive element.

Figure 1:
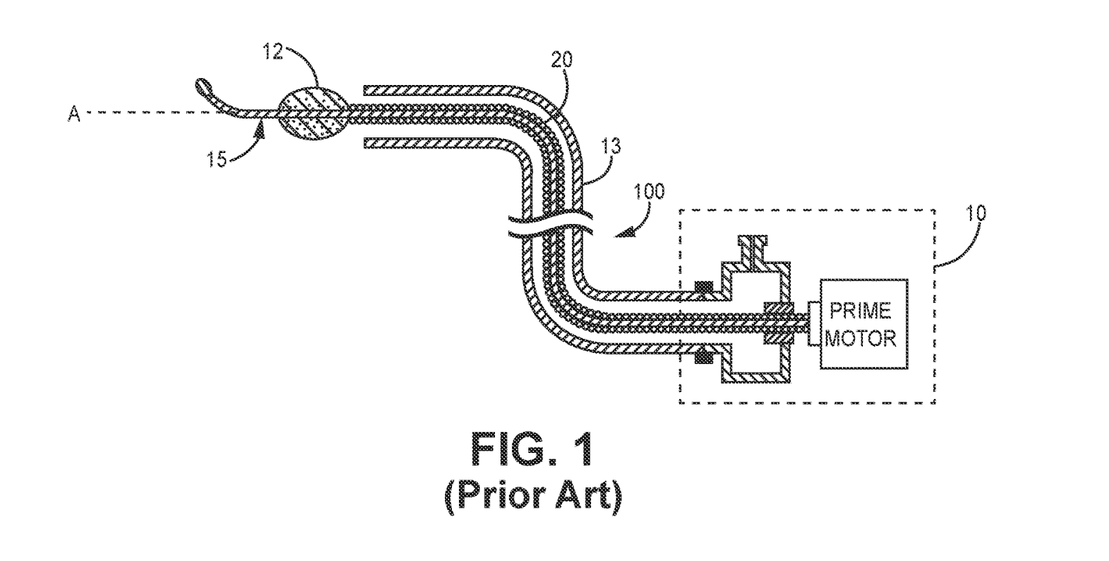
FIG. 1 is a cross-sectional view of a prior art device.

FIG. 1 illustrates a prior art device 100 comprising drive shaft 20 that is symmetric along its length. A symmetric and concentric burr 12 is mounted at the distal end of the drive shaft 20, wherein the burr 12 comprises a center of mass C that is located on the rotational axis A of the drive shaft 20. Drive shaft is translated within lumen of a catheter 13 and is connected at a proximal end to a prime mover located within a handle 10. Guide wire 15 is shown translated through the lumen of drive shaft 20 and through a lumen defined by burr 12. In this case, no asymmetry or eccentricity is present and, unless perturbed by bumping into an asymmetric object such as a lesion, the drive shaft 20 will not achieve orbital rotational motion as a result. Thus, the resting diameter of the drive shaft and of the burr will effectively be the same as the unperturbed working diameters of the drive shaft and of the burr during high-speed rotation.

Figure 2:
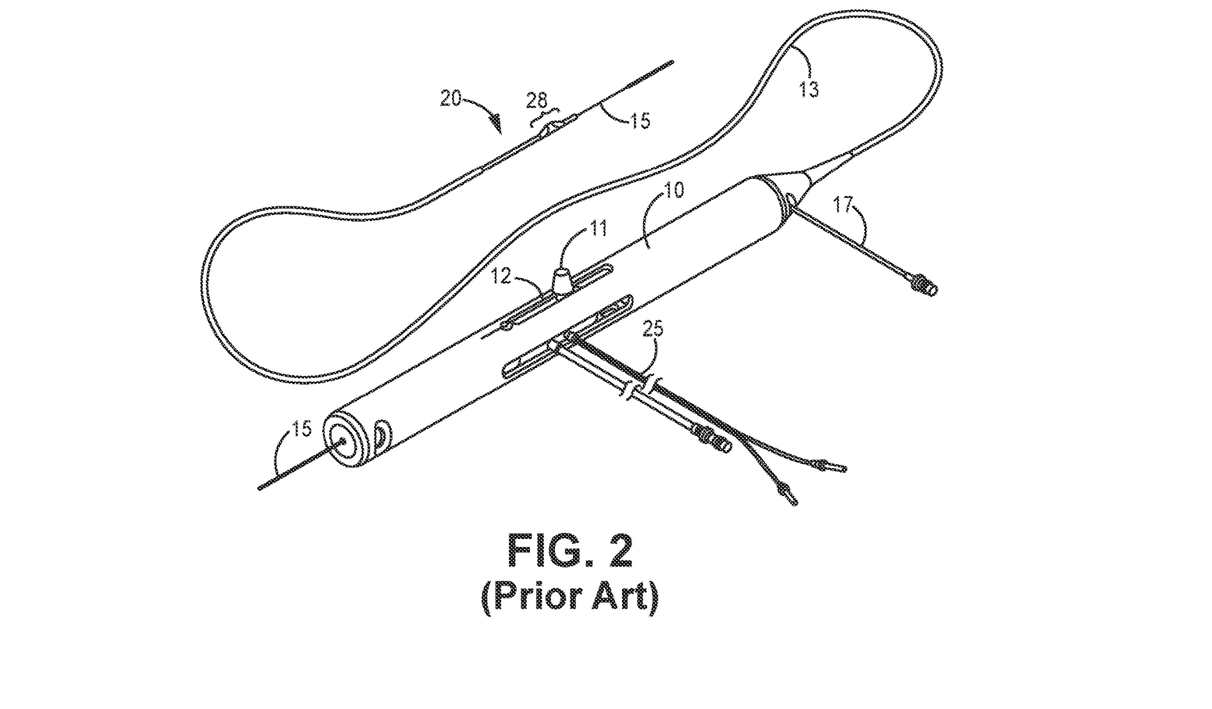
FIG. 2 is a perspective view of a prior art device.
Figure 3:
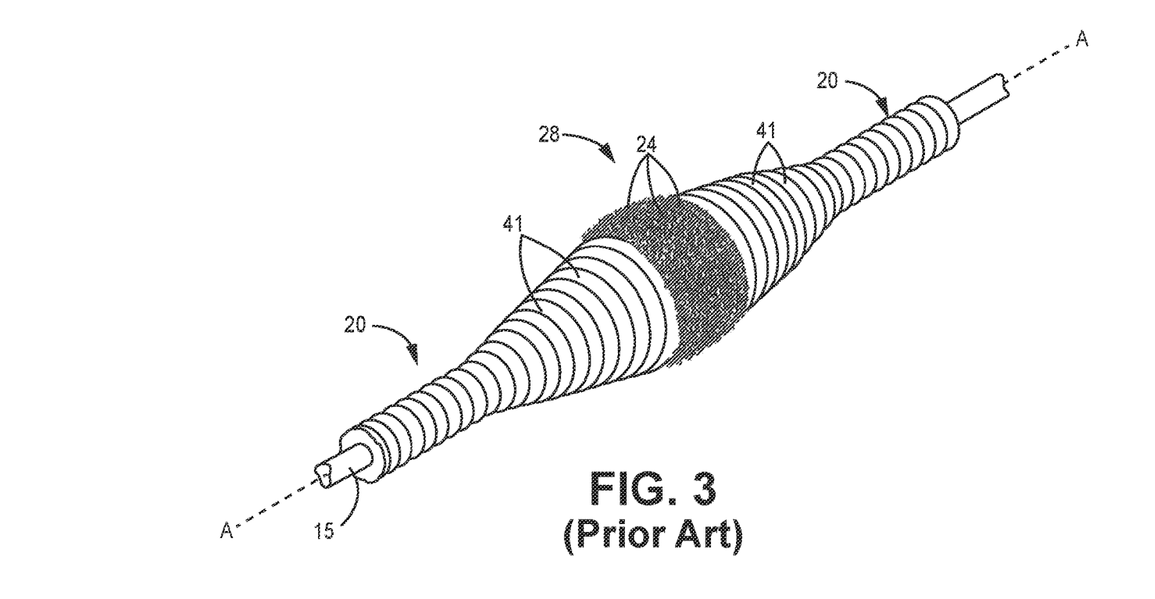
FIG. 3 is a perspective cutaway view of a prior art device.

The art progressed to form an enlarged and abrasive coated portion of the drive shaft as shown in FIGS. 2 and 3, wherein the wire turns of the drive shaft have been stretched by a shaped mandrel as is known in the art. The enlarged portion of the drive shaft may be symmetric and concentric in which case the center of mass will be located on the drive shaft's rotational axis and no orbital motion will result. Alternatively, the enlarged portion of the drive shaft may be asymmetric and eccentric wherein the center of mass is radially spaced away from the rotational axis of the drive shaft. The latter eccentricity results in generation of orbital motion of the eccentric enlarged drive shaft portion wherein the working diameter traced out by the enlarged portion is greater than its resting diameter.

Thus, FIG. 2, similar to FIG. 1, also provides a handle 10, an elongated flexible drive shaft 20 and an elongated catheter 13 extending distally from handle 10. The enlarged diameter portion 28 is formed from the wire turns of the drive shaft 20. Drive shaft 20 is formed or constructed from helically coiled wire turns. As known in the art, the drive shaft 20 may comprise one layer of helically coiled wire or two layers of helically coiled wire turns or filars as they are known in the art. In some cases, the two-layered embodiment of wire turns may comprise oppositely wound coils and in other cases the wire turns or filars of the two layers may be wound in the same direction. All such embodiments are within the scope of the present invention.

FIG. 2 further provides a guide wire 15 and a fluid supply line 17 for introducing a cooling and/or lubrication solution. A pair of optic cables 25 may be provided to monitor speed of rotation and the handle may include a control knob 11 the advance and/or retract the drive shaft.

FIG. 3 illustrates one embodiment of the enlarged drive shaft portion 28 of FIG. 2 in cutaway perspective view. Here, the enlarged wire turns or filars 41 of the drive shaft 20 are visible as is the exemplary abrasive coating 24 adhered thereto. As noted, the center of mass of enlarged portion 28 may be on the rotational axis A and, therefore concentric and not adapted to generate orbital motion during high-speed rotation. Alternatively the center of mass of enlarged portion 28 may be radially spaced away from the rotational axis A of the drive shaft 20 and thereby adapted to achieve orbital motion during high-speed rotation.

Figure 4:
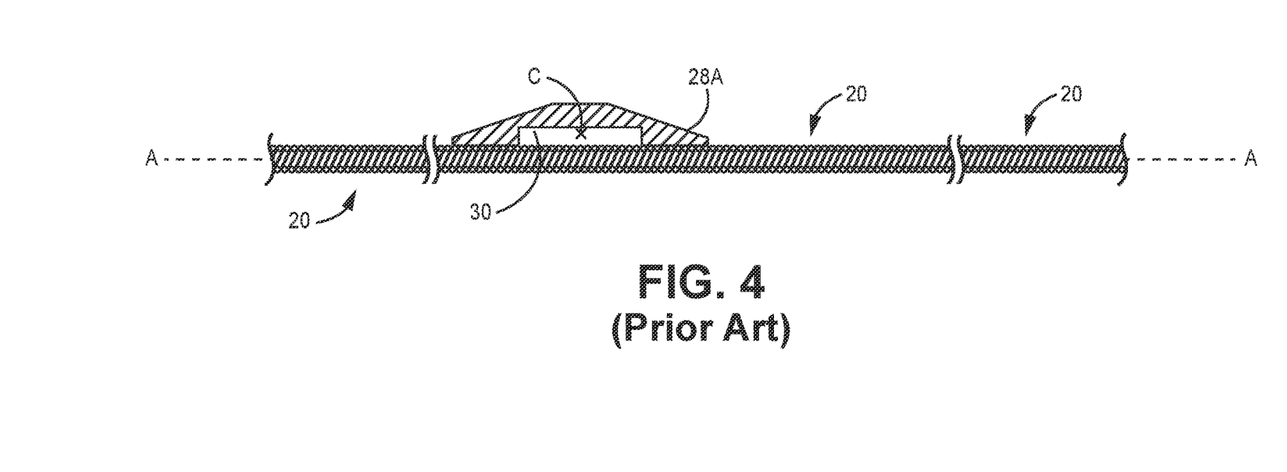
FIG. 4 is a cross-sectional and cutaway view of a prior art device.

FIG. 4 provides another alternative as known in the art wherein a crown 28A is mounted to the drive shaft 20. The crown 28A, as shown, is eccentric and/or eccentrically mounted to the drive shaft 28A to provide a center of mass C that is located radially away from the rotational axis A of the drive shaft 20. As with the eccentric embodiment discussed above in connection with FIGS. 3 and 4, the eccentric crown 28A will be urged into orbital motion during high-speed rotation of the drive shaft 20 wherein its working diameter traced out during rotation is greater than its resting diameter. The center of mass C location may be manipulated by modifying a number of elements as the skilled artisan will understand, including but not limited to the provision of a hollowed chamber 30 within the crown 28A. If present, the size and/or shaping of the hollowed chamber 30 may be changed to manipulate the center of mass C location.

Figure 5:
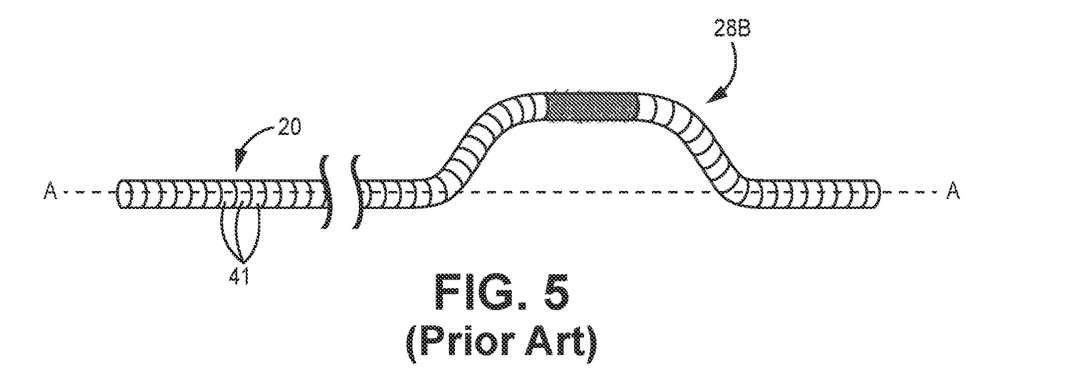
FIG. 5 is a cross-sectional and cutaway view of a prior art device.

A final exemplary prior art embodiment is illustrated in FIG. 5 wherein the desired eccentricity to generate orbital motion is provided by a pre-curved section 28B of the drive shaft 20. This arrangement radially spaces the center of mass C of the pre-curved section, and the accompanying abrasive section 24 which may be an abrasive coating as shown or a burr or crown attached thereto, away from the rotational axis A of the drive shaft 20. Consequently, high-speed rotation of this drive shaft 20 will result in a tracing of the abrasive section 24 having a working diameter that is great than its resting diameter.

Figure 6:
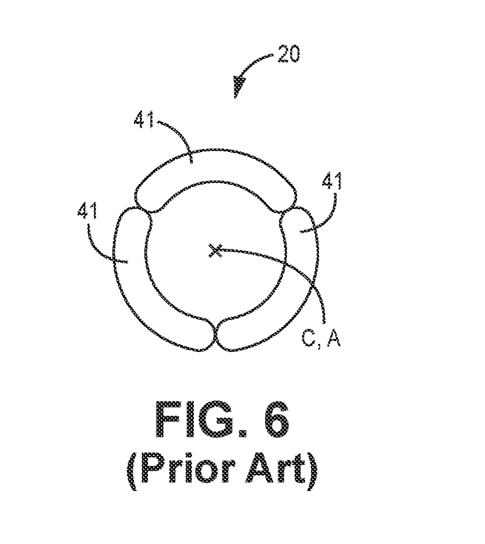
FIG. 6 is a cross-sectional view of a prior art drive shaft with guidewire.

FIG. 6 illustrates a cross-sectional view of the wire turns or filars 41 of a prior art drive shaft 20 and the defined lumen L therethrough. Generally, this prior art device is symmetric and concentric about the rotational axis and, therefore, the center of mass C at any point along the drive shaft's length will be located on the rotational axis A of the drive shaft and, without more, orbital motion will not be induced or achieved.

It would be desirable to provide a mechanism for achieving orbital motion and/or enhanced fluid flow at rotational speeds that are significantly lower than the known devices allow.

Various embodiments of the present invention address these, inter alia, issues.

Moreover, we provide disclosure of the following patents and applications, each of which are assigned to Cardiovascular Systems, Inc., and incorporated herein in their entirety, each of which may comprise systems, methods and/or devices that may be used with various embodiments of the presently disclosed subject matter:

U.S. Pat. No. 9,468,457, "ATHERECTOMY DEVICE WITH ECCENTRIC CROWN";
U.S. Pat. No. 9,439,674, "ROTATIONAL ATHERECTOMY DEVICE WITH EXCHANGEABLE DRIVE SHAFT AND MESHING GEARS";
U.S. Pat. No. 9,220,529, "ROTATIONAL ATHERECTOMY DEVICE WITH ELECTRIC MOTOR";
U.S. Pat. No. 9,119,661, "ROTATIONAL ATHERECTOMY DEVICE WITH ELECTRIC MOTOR";
U.S. Pat. No. 9,119,660, "ROTATIONAL ATHERECTOMY DEVICE WITH ELECTRIC MOTOR";
U.S. Pat. No. 9,078,692, "ROTATIONAL ATHERECTOMY SYSTEM";
U.S. Pat. No. 6,295,712, "ROTATIONAL ATHERECTOMY DEVICE";
U.S. Pat. No. 6,494,890, "ECCENTRIC ROTATIONAL ATHERECTOMY DEVICE";
U.S. Pat. No. 6,132,444, "ECCENTRIC DRIVE SHAFT FOR ATHERECTOMY DEVICE AND METHOD FOR MANUFACTURE";
U.S. Pat. No. 6,638,288, "ECCENTRIC DRIVE SHAFT FOR ATHERECTOMY DEVICE AND METHOD FOR MANUFACTURE";
U.S. Pat. No. 5,314,438, "ABRASIVE DRIVE SHAFT DEVICE FOR ROTATIONAL ATHERECTOMY";
U.S. Pat. No. 6,217,595, "ROTATIONAL ATHERECTOMY DEVICE";
U.S. Pat. No. 5,554,163, "ATHERECTOMY DEVICE";
U.S. Pat. No. 7,507,245, "ROTATIONAL ANGIOPLASTY DEVICE WITH ABRASIVE CROWN";
U.S. Pat. No. 6,129,734, "ROTATIONAL ATHERECTOMY DEVICE WITH RADIALLY EXPANDABLE PRIME MOVER COUPLING";
U.S. patent application Ser. No. 11/761,128, "ECCENTRIC ABRADING HEAD FOR HIGH-SPEED ROTATIONAL ATHERECTOMY DEVICES";
U.S. patent application Ser. No. 11/767,725, "SYSTEM, APPARATUS AND METHOD FOR OPENING AN OCCLUDED LESION";
U.S. patent application Ser. No. 12/130,083, "ECCENTRIC ABRADING ELEMENT FOR HIGH-SPEED ROTATIONAL ATHERECTOMY DEVICES";
U.S. patent application Ser. No. 12/363,914, "MULTI-MATERIAL ABRADING HEAD FOR ATHERECTOMY DEVICES HAVING LATERALLY DISPLACED CENTER OF MASS";
U.S. patent application Ser. No. 12/578,222, "ROTATIONAL ATHERECTOMY DEVICE WITH PRE-CURVED DRIVE SHAFT";
U.S. patent application Ser. No. 12/130,024, "ECCENTRIC ABRADING AND CUTTING HEAD FOR HIGH-SPEED ROTATIONAL ATHERECTOMY DEVICES";
U.S. patent application Ser. No. 12/580,590, "ECCENTRIC ABRADING AND CUTTING HEAD FOR HIGH-SPEED ROTATIONAL ATHERECTOMY DEVICES";
U.S. patent application Ser. No. 29/298,320, "ROTATIONAL ATHERECTOMY ABRASIVE CROWN";
U.S. patent application Ser. No. 29/297,122, "ROTATIONAL ATHERECTOMY ABRASIVE CROWN";
U.S. patent application Ser. No. 12/466,130, "BIDIRECTIONAL EXPANDABLE HEAD FOR ROTATIONAL ATHERECTOMY DEVICE"; and
U.S. patent application Ser. No. 12/388,703, "ROTATIONAL ATHERECTOMY SEGMENTED ABRADING HEAD AND METHOD TO IMPROVE ABRADING EFFICIENCY".

BRIEF SUMMARY OF THE INVENTION

Devices, methods and systems are described that enable achieving a working diameter that is greater than a resting diameter and to stimulate fluid circulation during high-speed rotation. The drag coefficient of the drive shaft is increased and, in some embodiments, the mass is increased. Among other advantages, the resulting drive shaft with an eccentric element integrated with and/or attached thereto will achieve orbital motion at a rotational speed that is less the rotational speed required to achieve orbital motion without the increased drag coefficient. The concomitant increase in fluid flow and/or fluid stirring at a comparatively lower rotational speed is a further advantage. Effectively, the increased fluid stirring ultimately increases the luminal orbiting frequency of the rotating system, and with a much faster rate of increase than known orbiting systems, when orbital motion is achieved across a wide range of rotational speed. These characteristics may allow, therefore, a smaller diameter abrasive element to be used which is advantageous in small and/or highly tortuous vessels.

The drag coefficient may be increased by a number of mechanisms including but not limited to the following:

Enhancing or adjusting the surface roughness of the externally facing surfaces of the drive shaft, e.g, the filars forming the drive shaft's construction;

Adding drag elements along the drive shaft in combination with a drive shaft adapted to achieve orbital motion via an eccentric abrasive element such as a crown or by other means including but not limited to those disclosed in co-pending application filed on even date herewith U.S. application Ser. No. 16/594,834, the disclosure of which is hereby incorporated by reference in its entirety.

These added drag elements may be placed proximal to and/or distal to the eccentric abrasive element when present and may comprise spring(s), coiled filar mass(es), paddle(s) or paddlewheel(s) or braid(s), bead(s), ringlet(s) and the like, and may be fixed to the drive shaft or may be free to rotate.

The figures and the detailed description which follow more particularly exemplify these and other embodiments of the invention.

DETAILED DESCRIPTION OF THE INVENTION

While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

Various embodiments of a rotational drive shaft for a rotational medical device such as a rotational atherectomy system are provided. Each embodiment generates orbital motion, derived from features integrated with the drive shaft not from an attached abrasive element.

Initially, it is to be understood that, as used herein and defined hereby, the word "eccentricity" and variants thereof refers to either (1) a difference in location between the geometric center of the drive shaft and the rotational axis of the drive shaft, or (2) a difference in location between the center of mass of the drive shaft and the rotational axis of the drive shaft.

Moreover, it is to be understood that, as used herein and defined hereby, the term "orbital motion" refers to the orbiting element, e.g., the drive shaft, achieving a working diameter that is larger than its resting diameter and wherein the orbital motion is induced by an eccentric element, such as a mass or eccentric abrasive element, mounted on or in or along the drive shaft, in certain embodiments integrated in, along or on the wire turns or filars of the drive shaft. The resulting movement of the drive shaft during orbital motion may also be referred to as a standing wave of predictable, customizable length and shape.

Mechanisms to Increase Drag Coefficient of a Drive Shaft Rotating in a Fluid.

1. Modifying or Adjusting the Surface Roughness

It is known that a surface's drag coefficient may be modified or adjusted to increase and/or decrease the surface roughness and may be measured by reference to, inter alia, the resulting Reynold's number. For example, if the Reynold's number is in the region of $4 \times 10^4$ to $4 \times 10^5$, then a smoother surface may result in a higher drag coefficient. Above a Reynold's number of $4 \times 10^5$, a rougher surface will likely result in a higher drag coefficient. Generally speaking, surface roughness will increase the drag coefficient in a turbulent flow environment for streamlined bodies. For bodies such as cylinders or spheres, an increase in the surface roughness may increase or decrease the drag coefficient depending on the Reynold's number.

Figure 7:
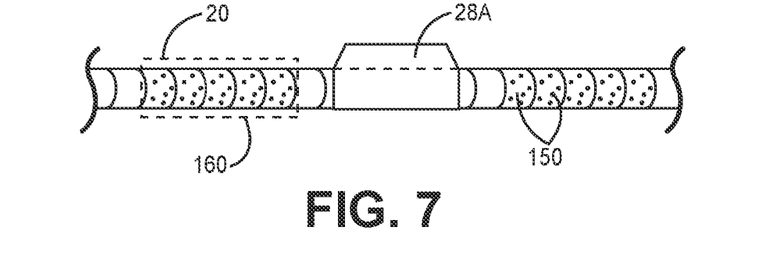
FIG. 7 is a cutaway view of one embodiment of the present invention.

For example, a laser or other device may be used to create surface imperfections 150 on at least a portion of the external surface of the drive shaft 20 comprising an exemplary eccentricity embodied as an abrasive element in the form of the eccentric crown 28A of FIG. 4 and as shown in FIG. 7. Generally surface imperfections may comprise pits or depressions in the external surface. Alternatively, some or all existing surface imperfections may be smoothed by application of an overlayer 160 such as a polymer overcoat or jacket (shown in dashed lines in FIG. 7). Depending on the Reynold's number of the subject drive shaft 20 spinning and orbiting through a fluid such as water, the drag coefficient may be increased which the skilled artisan will recognize will increase the tendency of the rotating drive shaft to achieve orbital motion.

Increasing the drag coefficient of a drive shaft 20 rotating in a fluid, by mechanisms described herein will, inter alia:

1. Enhanced rotational movement of the fluid in the environment of the rotating drive shaft 20 around the rotating drive shaft 20 as compared with a drive shaft 20 with a lower drag coefficient;
2. Achieve orbital motion at a lower rotational speed compared with a drive shaft having a lower drag coefficient as a result of the enhanced fluid circulation from No. 1 above, which will tend to move the drive shaft 20 off its rotational axis A and into orbital motion;
3. Achieve orbital motion at a lower rotational speed compared with a drive shaft 20 having a lower drag coefficient as a result of an increased pressure gradient driven by the enhanced fluid circulation of No. 1 above.

2. Adding Drag Elements Along the Shaft to Increase its Drag Coefficient.

Generally, drag elements may be added to the outside of the rotational drive shaft to increase its drag coefficient when rotating within a fluid. In some cases, as shown in FIG. 8, a drag element may comprise at least one spring 200 with an outer diameter D1 that is larger than the outer diameter D2 of the drive shaft 20 to which the at least one spring 200 is attached. The spring(s) 200 in this embodiment are preferably highly flexible so that the drive shaft's rigidity is not appreciably increased. Moreover, the spring(s) may be relatively light so that the mass increase attributable to the spring(s) is minimal. Thus, this embodiment functions to increase the drag coefficient primarily by the increased diameter and the surface "roughness" of the spring(s).

FIG. 8 provides therefore for a proximal spring 200P fixed to the drive shaft 20, proximally located relative to an eccentric abrasive element shown as an eccentric crown 28A operatively attached to the drive shaft 20. Further, an optional distal spring 200D is shown fixed to the drive shaft 20, distal to the eccentric crown 28A. In both cases the springs 200P, 200D are shown as spaced longitudinally away from the eccentric crown 28A. However, it will be understood that one or both springs 200P, 200D may contact the eccentric crown 28A and, therefore, not be spaced apart therefrom. Further, springs 200P and 200D are shown as circumferentially wrapped around drive shaft 20 when in operative connection therewith. Generally, springs 200P and 200D may be concentric, i.e., the center of masses $C_P$ and $C_D$ will be located on the axis of rotation A of drive shaft 20 along the lengths of spring(s) 200P and/or 200D and the eccentric crown's center of mass C will be radially offset from the axis of rotation A.

Alternatively, one or both springs 200P, 200D may be partially circumferentially wrapped around drive shaft 20. In this case, the center of mass at the partially wrapped spring will be radially offset from the drive shaft's rotational axis A along the length of the partially wrapped spring. FIG. 8B illustrates an exemplary drive shaft with partially wrapped proximal and distal springs 200P, 200D and the respective locations of the centers of mass CP, CD as well as the center of mass C location of eccentric crown 28A. Of additional note is the outer diameter D3 of the drive shaft 20 in combination with the partially wrapped springs 200P, 200D which is greater than the drive shaft's outer diameter D2. FIG. 8B illustrates an exemplary device wherein the centers of mass C, $C_P$ and $C_D$ are located along a common longitudinal plane, ie., there is no rotational angle between the centers of mass locations C, $C_P$ and $C_D$.

Figure 8A:
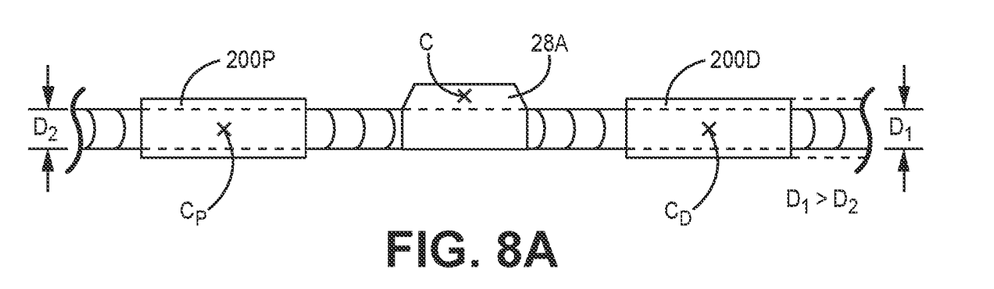
FIG. 8A is a cutaway view of one embodiment of the present invention.
Figure 8B:
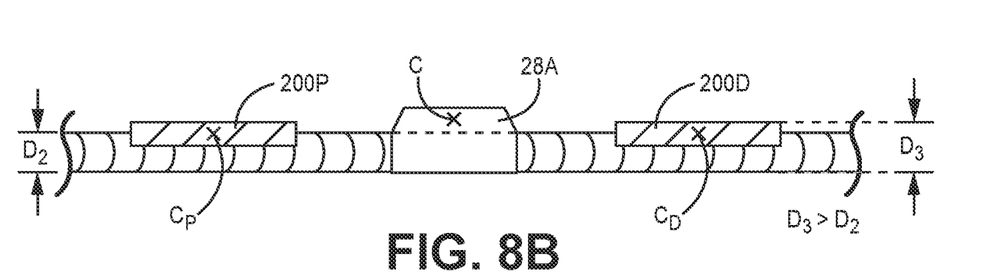
FIG. 8B is a cutaway view of one embodiment of the present invention.

The skilled artisan will recognize that the embodiment of FIG. 8A may be modified by increasing the mass of the spring(s) 200P, 200D in a radially asymmetric distribution to move one or both centers of mass $C_P$ and $C_D$ radially away from the axis of rotation A of drive shaft 20. These locations for centers of mass C, $C_P$ and $C_D$ may be along a common longitudinal plane, i.e., no rotational angle between the locations of centers of mass C, $C_P$ and $C_D$.

Figure 8C:
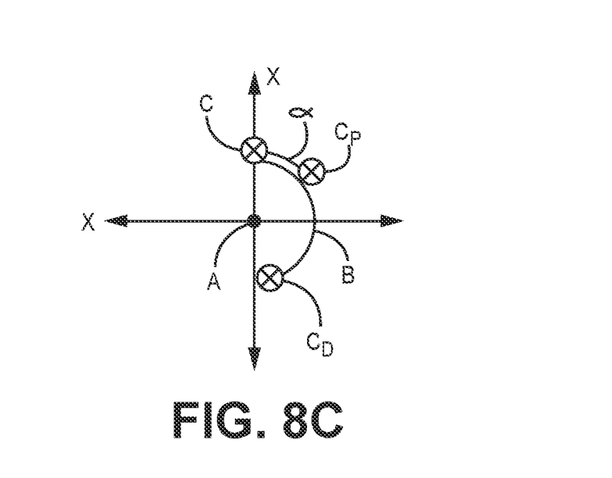
FIG. 8C is an end view along the rotational axis of a drive shaft of the present invention illustrating exemplary locations of centers of mass.

FIG. 8C illustrates exemplary locations for centers of mass C, $C_P$ and $C_D$ for either of the embodiments illustrated in FIG. 8A or 8B. Here, exemplary rotational angles α and β are provided between (1) the location of eccentric crown center of mass C and the proximal spring center of mass CP. and (2) the eccentric crown center of mass C and the distal spring center of mass CD, respectively. In these embodiments the centers of mass C, $C_P$ and $C_D$ may be longitudinally and rotationally spaced apart to, in combination with the increased diameters D1 and/or D3 to assist in stimulating orbital motion at lower rotational speeds than unmodified drive shafts.

In certain embodiments, therefore, the abrasive element, e.g., a crown, need not be eccentric and may instead be concentric with a center of mass on the rotational axis of the drive shaft 20, wherein the radially offset, and in some cases rotationally separated, center(s) of mass $C_P$ and/or $C_D$, in combination with the increased drag coefficient discussed above, drive the drive shaft 20 off axis and into orbital motion.

Finally, as shown in the Figures, generally it is preferable that the spring(s) $200_P$, $200_D$ comprise a length that is greater than the length of the eccentric abrasive element, i.e., eccentric crown 28A, to maximize and/or optimize the resulting drag increase. In other embodiments one or both of the spring(s) $200_P$, $200_D$ may be of equal length or may comprise lengths that differ. Moreover, the lengths of spring(s) $200_P$ and/or $200_D$ may be the same as, or less than, the length of the eccentric crown 28A or eccentric abrasive element.

The embodiment illustrated in FIG. 8A will be discussed further infra.

Working Example 1

The proximal and distal springs $200_P$, $200_D$ of FIG. 8A were placed on the proximal and distal sides of a 1.25 mm eccentric crown 28A along the rotational drive shaft 20 as shown in FIG. 8 (modified device) and then rotated at various speeds. The known rotational drive shaft 20 and 1.25 mm eccentric crown 28A without springs were then rotated at the same speeds (unmodified device) Both sets of conditions were monitored for orbital motion frequency at the tested rotational speeds.

Figure 9:
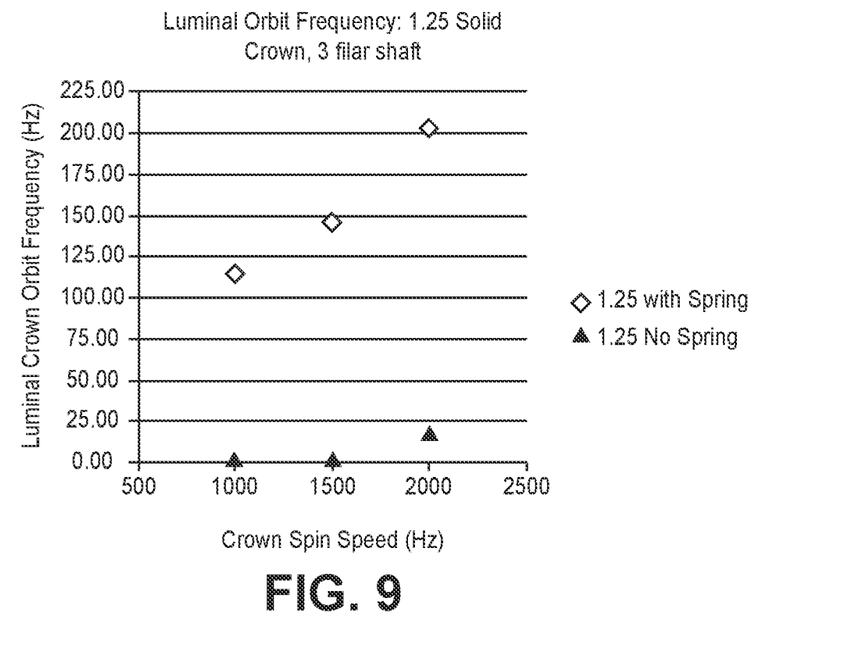
FIG. 9 is a graphic illustration of a working example of one embodiment of the present invention.

FIG. 9 illustrates the measured results of Working Example 1.

The unmodified device, i.e., without springs, failed to achieve orbital motion at a relatively low speed (1000 Hz) or at a medium rotational speed (1,500 Hz), only achieving a very low frequency orbiting motion at the designated high speed of 2,000 Hz.

On the other hand, the modified device produced orbital motion, and at a much higher orbiting frequency, at all tested speeds. The data indicates a linear relationship between rotational speed and orbiting frequency.

One of the most significant conclusions based on these data is that the addition of the springs $200_P$, $200_D$ having a relatively low mass but with an outer diameter D1 greater than the outer diameter D2 of the drive shaft 20, increased the drag coefficient of the drive shaft 20 which, in turn, induced orbital motion at a significantly lower rotational speed and with significantly greater orbital frequency than the unmodified drive shaft and eccentric crown combination.

Accordingly, drag elements as used herein may comprise a diameter increase over the diameter of the drive shaft 20 as a mechanism to achieve increased drag coefficient and, as a result, orbital motion with greater frequency at a lower rotational speed than possible in known devices or systems.

There are many possible mechanisms to increase a drive shaft's drag coefficient and that may rely on increasing the drive shaft's outer diameter as in the working example and/or with an increase in mass and/or relative locations of the resultant centers of mass. Additional exemplary drag elements that may be added to the drive shaft to increase drag coefficient follow.

2A. Add a Drag Element(s) Non-Rotationally Fixed to the Shaft

Figure 10A:
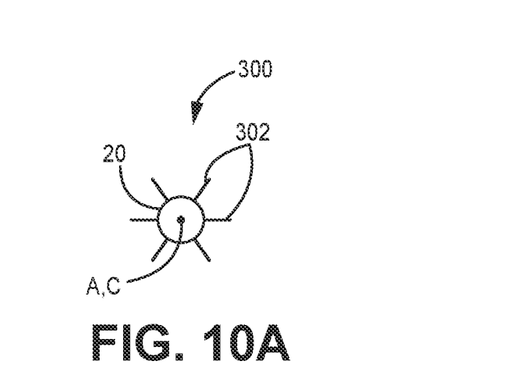
FIG. 10A is a front view of one embodiment of the present invention.
Figure 10B:
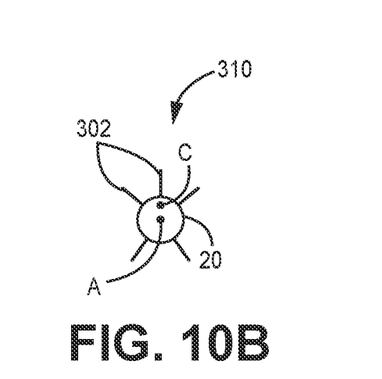
FIG. 10B is a front view of one embodiment of the present invention.
Figure 10C:
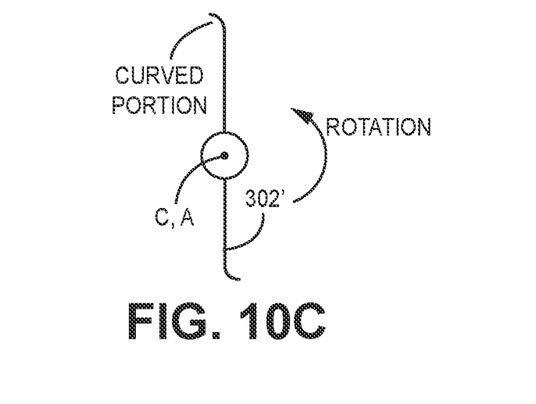
FIG. 10C is a front view of one embodiment of the present invention.

An exemplary drag element may be added to the drive shaft 20 that has arms, or radial projections 302, extending radially outwardly as shown in FIGS. 10A-10C as an exemplary paddlewheel 300 (FIG. 10A). However, any drag element comprising a radial projection, wherein the radial projection(s) may either be straight and/or curved and/or cupped to further enhance fluid circulation, will work to increase the drag coefficient.

FIG. 10A provides a symmetrical set of radial projections 302, wherein the center of mass C will be on the rotational axis A of the drive shaft 20 when attached thereto. In this case, the drag coefficient and resultant urging of the drive shaft 20 into orbital motion is due to increased fluid flow during rotation. The adjacent radial projections 302 are equally spaced apart around the drive shaft 20. An alternative may comprise unequal spacing between adjacent radial projections 302.

FIG. 10B comprises asymmetric distribution of the radial projections 302 around the paddlewheel drag element 320 so that the center of mass C is now radially offset from the drive shaft's nominal or resting axis of rotation A, thus contributing to achieving orbital motion, in addition to enhanced fluid flow.

Finally, FIG. 10C provides an exemplary set of cupped or curved radial projections 330 that may be symmetrically or asymmetrically distributed around the drive shaft 20 with center of mass located on, or located radially away from, respectively, the drive shaft's rotational axis A.

Further asymmetry, and resulting radially offset center of mass relative to the axis of rotation A, may achieved in the embodiments of FIGS. 10A-10C by modifying some of the radial projection lengths so that they are not all equal and/or increasing the mass of one or more of the radial projections.

The embodiments of FIGS. 10A-10C may be non-rotationally fixed to the drive shaft 20. One or more of these drag elements may be fixed to the drive shaft 20. When an eccentric abrasive element is attached to the drive shaft, one or more drag elements may be affixed proximal to and/or distal to the eccentric abrasive elements. When the drive shaft comprises eccentricity derived from other means such as in the drive shaft filar construction itself or inserted plugs of mass within a filar(s), the drag element(s) may be similarly affixed proximal and/or distal to the region of eccentricity integrated into the drive shaft 20.

Alternatively, drag elements comprising radial projections may be formed from the external surface of individual filars 41 of the drive shaft 20, wherein the drag elements extend therefrom. As described above, the radially projecting drag elements may be permanently radially extended away from the drive shaft 20 or may comprise a biased flattened profile until the drive shaft 20 is rotated at a threshold speed which causes the drag elements to extend radially and affect the drag coefficient.

Adjustment of the drag coefficient may be made by the surface area of individual radial projections of the drag element(s), the number of radial projections on each drag element, the shape and/or curvature of the radial projection(s). Moreover, the radial projection(s) may be adapted to achieve a working configuration whereby the radial projections are biased to lie substantially flat against the outer surface of the drive shaft 20 and/or coiled around the drive shaft 20. Rotation of the drive shaft 20 may then move the radial projections into their working position to achieve the working configuration.

2B. Add a Drag Element(s) Rotationally Operationally Attached to the Shaft

This embodiment for increasing or adjusting to optimize drag coefficient is similar to that of FIG. 10A-10C except that the radial projection embodiments may be rotationally operationally attached to the drive shaft 20.

2C. Increasing Mass and Outer Diameter Along the Drive Shaft

Increasing the mass along the drive shaft 20 will increase the centrifugal force that holds the orbiting drive shaft's standing wave in place and accentuating the magnitude of the orbiting shaft's 20 deflection or working diameter. The greater the orbiting diameter, or deflection, the more fluid will be rotatingly circulated, thus generating orbital motion at lower rotational speeds than unmodified known drive shafts. Exemplary mechanisms to increase mass for the stated purposes follow:

Coiled Wire or Filar Mass Element Attached to the Shaft with Eccentric Crown.

Figure 11:
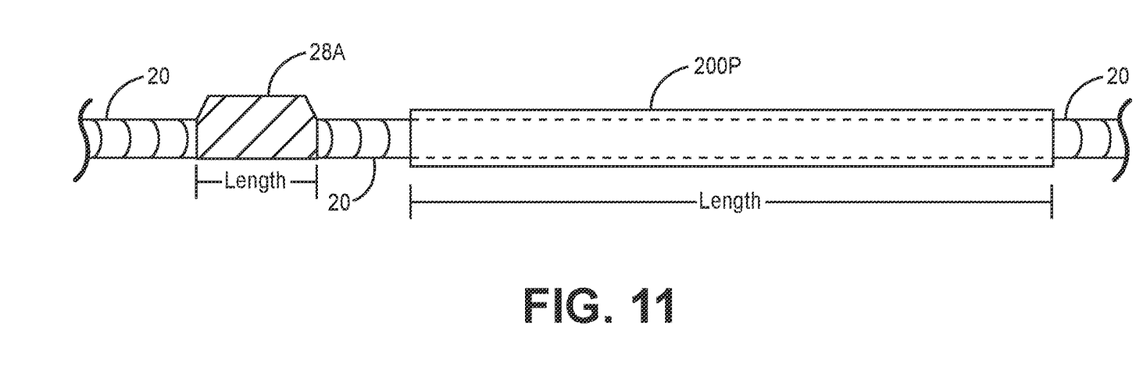
FIG. 11 is a cutaway view of one embodiment of the present invention.

In combination with an eccentric crown, a drag element comprising a coiled wire or filar mass or spring 200, e.g., a wound spring, may be placed over or around at least a part of the drive shaft 20 at point(s) distal to and/or proximal to the eccentric crown 28A. In all cases, Applicant has found that the best results are obtained by placement of the mass or spring 200 within close proximity of the eccentric crown 28A. Most preferably, at least the proximal and/or distal mass(es) or spring(s) are in touching contact with the eccentric crown. FIG. 11 illustrates this arrangement where an exemplary proximal spring $200_P$ comprises a length that is longer than the length of the eccentric crown 28A attached to the drive shaft 20. There is no distal drag element or spring $200_D$ attached in this exemplary illustration. The proximal spring $200_P$ may comprise a length that is at least more than twice the length of the eccentric crown 28A and, as in FIG. 11, may comprise a length that is 5 times or more the length of the eccentric crown 28A. The drag element shown as a spring $200_P$ may also take the form of a coiled filar mass or other similar structure.

Working Example 2

As seen in FIG. 11, a the proximal spring $200_P$ is placed on the drive shaft 20 proximal to and spaced from the eccentric crown 28A (modified device) and compared with a drive shaft 20 comprising only the eccentric crown 28A (unmodified device).

Figure 12:
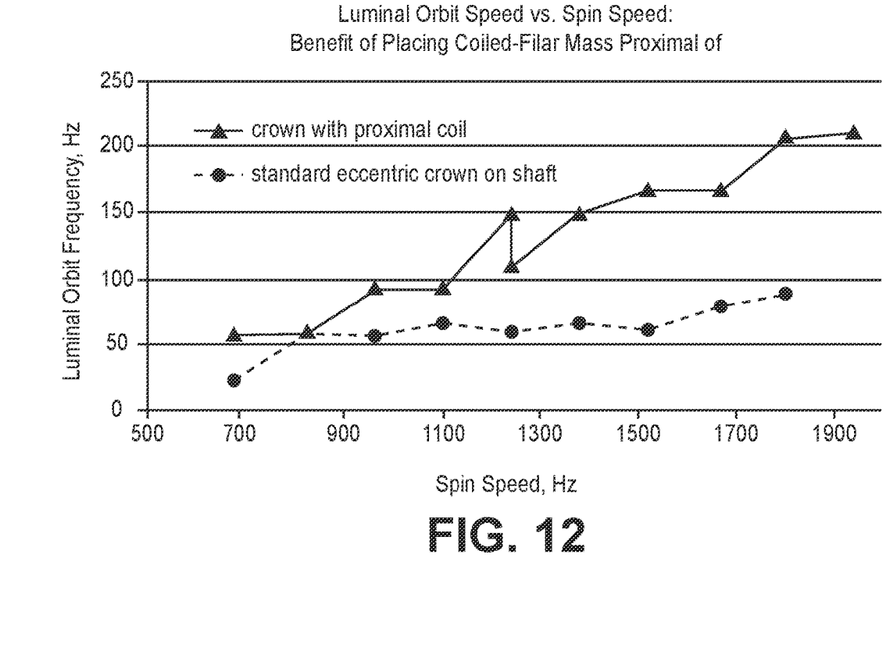
FIG. 12 is a graphic illustration of a working example of one embodiment of the present invention.

The results for Working Example 2 are shown graphically in FIG. 12.

The unmodified device achieves a very low frequency of orbiting (approximately 20 Hz) at an approximate rotational speed of 700 Hz, with a very slow, low rate of increase, reaching a maximum orbiting frequency of about 90 Hz at a rotational speed of about 1850 Hz.

On the other hand, the modified device reached an orbiting frequency of just over 50 Hz at the lowest rotational speed of about 700 Hz and illustrates a must higher rate of increase in orbiting frequency than the unmodified device. The modified device reaches an orbiting frequency of just over 200 Hz at a rotational speed of about 1850 Hz.

As can be seen, the addition of the proximal drag element $200_P$ increases orbiting frequency at any given rotational speed as compared with the unmodified device and induces orbital motion at a lower rotational speed compared with the unmodified device.

Coiled Wire or Filar Mass Element Attached to the Drive Shaft without Eccentric Crown The coiled wire or filar coil or spring drag element may be partially wrapped around drive shaft 20 and/or may comprise an eccentric or asymmetric radial mass distribution as discussed above, to provide the necessary eccentricity by moving the local center of mass C radially off of the rotational axis and enabling inducement of orbital motion during high-speed rotation. In either case, the drag element's material may preferably a dense material such as tungsten, i.e., denser than the drive shaft's material which may be stainless steel. Alternatively a medium density material such as stainless steel or even a relatively low density material such as titanium (less dense than the drive shaft's material) may be employed. The wire or filars of the drag element and/or at least some of the external surfaces of the drive shaft wire turns or filars 41 may be coated with an abrasive in this embodiment.

In other embodiments, the addition of the mass, and increased outer diameter, of the drag element(s) will be sufficient to induce orbital motion, particularly when the drag elements are spaced longitudinally apart.

Braided Mass Element Disposed on Drive Shaft with Eccentric Crown

Another drag element comprising a mass may comprise a braided structure that is wrapped at least partially around the drive shaft proximal and/or distal to the eccentric crown. As with the spring 200 embodiment, braided drag element may be concentric and with a center of mass on the drive shaft's axis of rotation, or may be eccentric and comprising an asymmetry of mass may be introduced by an eccentric or asymmetric radial mass distribution in the braided element or by partially wrapping around the drive shaft 20.

Braided Mass Element Disposed on Drive Shaft without Eccentric Crown

The braided mass drag element may be partially wrapped around drive shaft 20 to provide the necessary eccentricity by moving the local center of mass C radially off of the rotational axis and enabling inducement of orbital motion during high-speed rotation as discussed above. In this case, an eccentric abrasive element or, e.g., a crown 28A may not be required. The braids of the braided mass element and/or at least some of the external surfaces of the drive shaft wire turns or filars 41 may be coated with an abrasive in this embodiment.

As above, in certain embodiments, the addition of the mass, and increased outer diameter, of the braided mass drag element(s) will be sufficient to induce orbital motion, particularly when more than one braided drag element is provided and spaced longitudinally apart.

For reasons described herein, this and all embodiments discussed herein, may induce the drive shaft 20 to achieve orbital motion with need or aid of an eccentric abrasive element such as an eccentric crown 28A.

Bead(s) Disposed on Drive Shaft with Eccentric Crown

Figure 13:
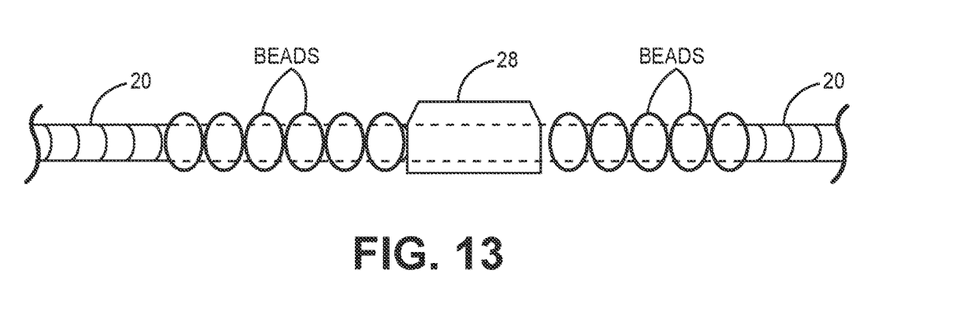
FIG. 13 is a cutaway view of one embodiment of the present invention.

Alternatively, as shown in FIG. 13, one or more beads may be attached to the drive shaft proximal to and distal to the exemplary eccentric abrasive element, the eccentric crown 28A. The beads adjacent to the crown 28A may be in touching contact with the crown 28A or may be spaced away from the crown 28A. When more than one bead is provided proximally and/or distally from the crown 28A, adjacent beads may be in touching contact or may be spaced apart. The adjacent beads are not fixed to each other to preserve flexibility. The number of beads proximal to the eccentric crown 28A may be equal to or may be different than the number of beads distal to the eccentric crown 28A. As shown, beads of equal mass are used, though the unequal masses may be used. Further, in FIG. 13, 6 proximal beads and 5 distal beads are shown, wherein all the beads are of equal mass, thus the total distal mass of all distal beads is greater than the total proximal mass of all proximal beads.

Bead(s) Disposed on Drive Shaft without Eccentric Crown

Similar to other embodiments described above, the proximal and/or distal beads may be eccentric (through mass or mounting or geometry), or concentric and produce a resultant center of mass that is either radially located away from the axis of rotation of the drive shaft or located on the axis of rotation, respectively. In either case, the drive shaft 20 may be induced to orbital motion without need or aid of an eccentric abrasive element such as the exemplary crown 28A for reasons described herein.

As with other drag elements discussed herein, bead(s) may be non-rotationally or rotationally operationally attached to the drive shaft. Bead(s) may be spherical or of a non-concentric geometric shape.

Low-Profile Ringlets Disposed on the Drive Shaft with/without Eccentric Crown

Figure 14:
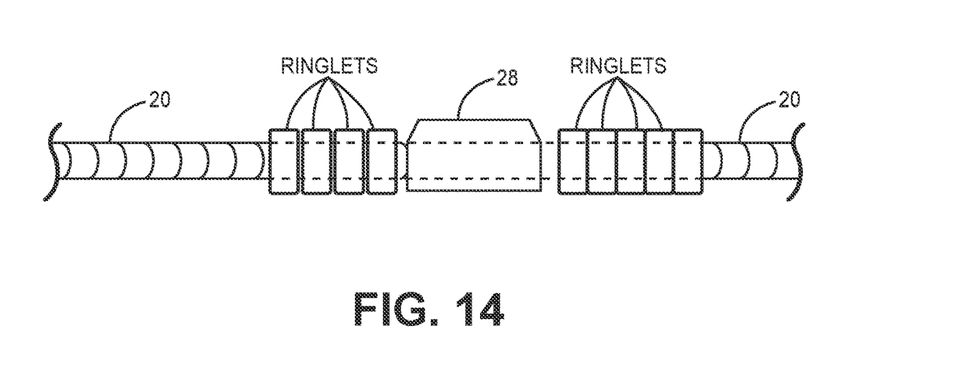
FIG. 14 is a cutaway view of one embodiment of the present invention.

FIG. 14 shows a modification of FIG. 13 in that ringlets are used instead of beads. All other features, alternatives and functionality described in connection with FIG. 13 apply to the modified ringlets of FIG. 14.

Figure 15A:
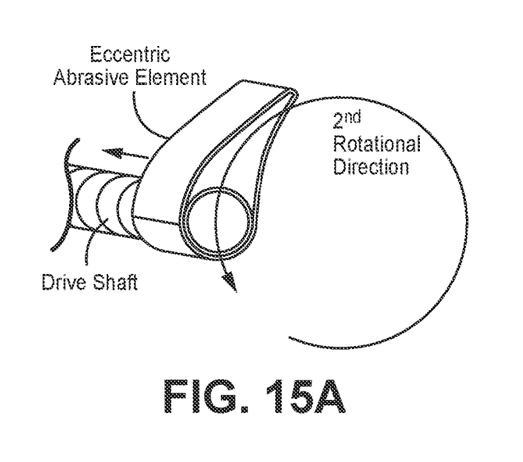
FIG. 15A is a perspective view of one embodiment of the present invention.
Figure 15B:
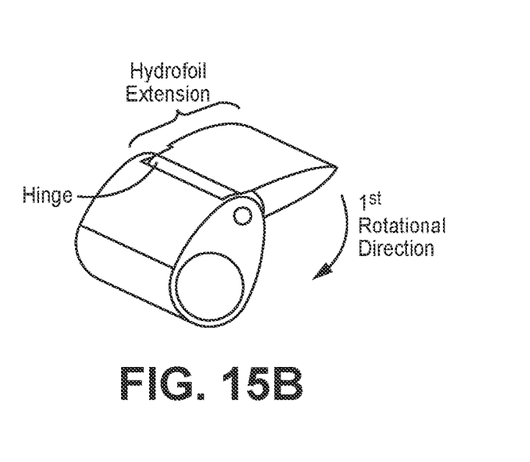
FIG. 15B is a perspective view of one embodiment of the present invention.

Hinged Hydrofoil to Increase Drag Coefficient of Rotational Drive Shaft and Having Delivery and Working Configurations Finally, FIGS. 15A and 15B illustrate another application of hydrodynamic principles to force a rotating abrasive element attached to a rotational drive shaft off of a concentric rotating spin and drive the abrasive element into orbital motion wherein the working diameter traced during high-speed rotation is larger than its resting diameter. FIG. 15 thus illustrates a hydrofoil abrasive element that, when attached to the drive shaft 20 and rotated at a threshold rotational speed will induce orbital motion. The maximum diameter of the hydrofoil abrasive element may be reduced for delivery through a sheath or delivery catheter, and to accommodate smaller and/or tortuous vessels, by providing a flex point, e.g., a hinge as shown enabling the hydrofoil extension to fold around the body of the hydrofoil abrasive element. Once delivered out of the delivery catheter or sheath lumen, the hydrofoil extension element may be induced to expand by rotating the drive shaft in a first rotational direction. Once the hydrofoil extension is expanded by force of fluid and rotating within the fluid, and secured into the working position, the drive shaft may be rotated in the second opposite rotational direction where hydrodynamics causes orbital motion. Alternatively the hydrofoil extension hinge may be biased to expand to the working position.

Alternatively, the hydrofoil extension may comprise a shape memory material that is biased to expand into the working position so that the hydrofoil extension may be collapsed within the lumen of a delivery catheter or sheath for delivery at a low profile, then upon delivery out of the lumen of the catheter or sheath, the hydrofoil extension will biasingly expand to enable rotation and inducement of orbital motion. Hydrofoil extension may be recollapsed for withdrawal by proximally moving the hydrofoil abrasive element into the catheter or sheath lumen.

The descriptions of the embodiments and their applications as set forth herein should be construed as illustrative, and are not intended to limit the scope of the disclosure. Features of various embodiments may be combined with other embodiments and/or features thereof within the metes and bounds of the disclosure. Upon study of this disclosure, variations and modifications of the embodiments disclosed herein are possible, and practical alternatives to and equivalents of the various elements of the embodiments will be understood by and become apparent to those of ordinary skill in the art. Such variations and modifications of the embodiments disclosed herein may be made without departing from the scope and spirit of the invention. Therefore, all alternatives, variations, modifications, etc., as may become to one of ordinary skill in the art are considered as being within the metes and bounds of the instant disclosure.

What is claimed is:

1. A rotational medical device having a prime mover that is operationally rotationally connected to a drive shaft having an axis of rotation and that is adapted to achieve a working diameter along a portion of the drive shaft that is greater than its resting diameter during high-speed rotation, the rotational medical device further comprising:
    an abrasive element operatively attached to the portion of the drive shaft and comprising a center of mass that is radially offset from the drive shaft's axis of rotation for achieving the working diameter of the portion of the drive shaft during rotation of the drive shaft;
    surface imperfections created on at least the portion of the external surface of the drive shaft, wherein the surface imperfections are created proximal to and/or distal to the abrasive element and wherein the surface imperfections are adapted to increase a rotational drag coefficient of the drive shaft during rotation of the drive shaft by the prime mover.

2. The rotational medical device of claim 1, further comprising a polymer overlayer covering at least part of the external surface of the drive shaft to adjust the drag coefficient of the drive shaft.

3. The rotational medical device of claim 1, wherein the surface imperfections are created by a laser device.

4. The rotational medical device of claim 1, wherein the surface imperfections are created proximal to the abrasive element.

5. The rotational medical device of claim 1, wherein the surface imperfections are created distal to the abrasive element.

6. The rotational medical device of claim 1, wherein the surface imperfections are created proximal to and distal to the abrasive element.

* * * * *